United States Patent

Bumann

[11] Patent Number: 6,103,755
[45] Date of Patent: Aug. 15, 2000

[54] FOODSTUFF WITH PROPHYLACTIC AND/OR HEALING EFFECT AND PROCESS FOR ITS PRODUCTION

[76] Inventor: Harold Bumann, Chalet Felsschlosschen, CH-3906 Saas-Fee, Switzerland

[21] Appl. No.: 08/910,751

[22] Filed: Aug. 13, 1997

Related U.S. Application Data

[62] Division of application No. 08/212,313, Mar. 14, 1994, which is a continuation of application No. 07/820,889, Jan. 17, 1992, abandoned.

[30] Foreign Application Priority Data

| May 22, 1990 | [CH] | Switzerland | 1745/90 |
| May 25, 1990 | [CH] | Switzerland | 1783/90 |
| May 25, 1990 | [CH] | Switzerland | 1784/90 |

[51] Int. Cl.[7] .......... A61K 31/355; A61K 31/34; A61K 31/22; A61K 31/20; A61K 31/07
[52] U.S. Cl. .......... 514/458; 514/474; 514/549; 514/560; 514/725
[58] Field of Search .................. 514/458, 474, 514/549, 560, 725

[56] References Cited

U.S. PATENT DOCUMENTS

| 4,737,367 | 4/1988 | Langer et al. . |
| 4,874,603 | 10/1989 | Fratzer . |
| 4,963,380 | 10/1990 | Schroeder et al. . |
| 5,120,760 | 6/1992 | Horrobin . |

FOREIGN PATENT DOCUMENTS

| 4380589 | 5/1990 | Australia . |
| 0108594 | 5/1984 | European Pat. Off. . |
| 3213744 | 11/1982 | Germany . |
| 2140806 | 12/1984 | United Kingdom . |
| 2209936 | 6/1989 | United Kingdom . |
| 8905101 | 6/1989 | WIPO . |

OTHER PUBLICATIONS

Remington's Pharmaceutical Sciences 16th Edition (1980) pp 627–8.
R.H. Garrison et al., "The Nutrition Desk Reference"; 1985 by Keats (Connecticut) pp 166–171.
Free radical tissue damage: protective role of antioxidant nutrients; by L.J. Machlin et al., FASEB J. 1: 441–445, 1987.

*Primary Examiner*—Raymond Henley, III
*Attorney, Agent, or Firm*—George Pappas

[57] ABSTRACT

The novel foodstuff contains at least one combination of at least polyunsaturated omega-3-fatty acid and/or its esters and one or more vitamins and/or pro-vitamins. If taken continuously, the foodstuff has prophylactic and/or curative effects and is therefore suitable for the prevention and/or cure of civilisation-induced diseases, especially cardiovascular diseases and cancer. It is preferably provided in the form of a drink based on fruit and/or vegetable juice preferably containing eicosapentaenoic acid and/or docosahexaenoic acid or their esters as the omega-3-fatty acid. The vitamin component is preferably made up of beta-carotene, vitamin C and vitamin E. The fatty and fat-soluble components are preferably used in the form of a dry powder in making the foodstuff. The foodstuff is distinguished by its agreeable flavour, pleasant odour, attractive appearance and good shelf life and its effects and the aforementioned qualities therefor remain unchanged even after several months' storage.

14 Claims, No Drawings

FOODSTUFF WITH PROPHYLACTIC AND/OR HEALING EFFECT AND PROCESS FOR ITS PRODUCTION

This application is a division of application No. 08/212,313, filed Mar. 14, 1994, which is a continuation of application No. 07/820,889 filed on Jan. 17, 1992 now abandoned.

The invention concerns a foodstuff which at continued ingestion has as prophylactic and/or healing effect for prevention and/or healing of certain diseases, mainly diseases of civilization caused by an unhealthy way of nutrition, abuse of alcohol and nicotine and by an increasing environmental burden, for instance cardiovascular diseases, e.g., heart infarct and arteriosclerosis, as well as cancer. The foodstuff is preferably available in the form of a beverage, for instance on the basis of fruit and/or vegetable juice.

Nobody will doubt the significance and importance of prophylaxis, the prevention of diseases. Nonetheless, observance, knowledge, acceptance and realization on the part of the public and, concomitantly caused thereby, the status of research in this field, unfortunately, have so far not been adequate yet. In several countries, among others in Switzerland, multiple year research projects in this direction have been initiated. On the part of the public, especially in the industrialized countries, mentality, convenience and habits represent major obstacles. In general, present matters are more significant to the people in these countries than matters of the future and thoughts of the possibility or probability of a future, serious illness are dismissed. The nutritional habits lead to an excessive ingestion of foodstuffs which in the long run are harmful, for instance saturated fatty acids, respectively fats containing glycerides, and of carbohydrates. Additionally, much of what the apostles of a so-called healthy nutrition recommend to the public is in part cumbersome to prepare and in part anything but attractive or tasty.

It is known that multiple unsaturated fatty acids, specifically multiple olefinic omega-3-fatty acids, which in the form of their glycerin esters are ingredients of fish oil and liver oil, also known as cod liver oil, which dependent on fish type and location of catch amount to 20–33% of the total amount of fat in fish oil, protect from cardiovascular diseases, such as heart infarct and arteriosclerosis and, as can be presumed on the basis of recent studies, promise a prophylactic effect against cancer. Studies, for example of nutritional habits of Greenland eskimos, who consume large amounts of fish, confirm these effects. Similar findings were made in Japan, where fish as well represents an essential part of the diet. A long-time study in Holland has shown that the consumption of only 30 grams of fish per day causes a 50% reduction in coronary mortality as compared to control persons not eating fish. Furthermore, clinical tests proved unequivocally that the following effects were achieved through the regular ingestion of fish oil with a content of eicosanoic pentaene acid and docosanoic hexaene acid over extended periods of time:

lowering of the triglyceride and cholesterol level;
 improvement of the flow properties of the blood;
 reduction of thrombocyte aggregation (blood curdling);
 lowering of the blood flow resistance.

Despite these known, favorable effects of fish oil and its ingredients, demand for these products is extremely low, which doubtless is attributable to the repulsive taste of fish oil and cod liver oil. In this context it is recalled that in olden times young people, from infancy to adolescence, were forced to swallow daily two to three teaspoonfuls of "cod liver oil," of which persons exposed to this procedure and still living today shudder to think. Owing to its caloric richness, its easy resorbability and its high vitamin content, cod liver oil was considered, so to speak, as a panacea against a poor nutritional status, scrofulosis, chronic infections, keratomalacia, growth and developmental disturbances and against deficiencies in pregnancy. Contrarily, the cardiovascular effects were then hardly paid any attention. Based on recent insights, the cardio-vascular effects and the prophylactic effect against cancer that can be safely expected have now advanced into the foreground. But the repulsive taste of fish oil or cod liver oil stands in the way of a "voluntary" regular ingestion just as does the tendency to cause in the consumer an unpleasant eructation after ingestion. Additionally, the effective omega-3-fatty acids concerned-are in pure form, for instance produced by extraction, presently not available in sufficient quantities and at reasonable prices. To counteract the abstinence caused by the repulsive taste, fish oil recently has been offered in capsule form at pharmacies. Apart from the high price caused thereby, this leads to an underdosing, since the content of a single capsule is insufficient to unfold the desired prophylactic and/or healing effect; but the ingestion of several such capsules is considered an unreasonable expectation by many, all the more so as a retroactive, unpleasant eructation cannot be ruled out.

Moreover, studies have shown that multiple olefinically unsaturated fatty acids also display a prophylactic anticancer effect. Considerably better known and reinforced by studies, however, is the fact that the risk of cancer can be reduced by certain vitamins, for instance vitamin E, vitamin A, especially its beta-carotene precursor, and vitamin $A_1$ (retinol) as well as vitamin C. These vitamins thus represent effective adjuvants for the prophylaxis and therapy of cancer. However, it should be noted that the effect of the various vitamins differs depending on genesis, pathology and location of the occurrence of various cancer types, and that a single vitamin normally displays the desired effect only with a specific type of cancer.

Therefore, the problem underlying the invention is to provide a food-stuff of the initially mentioned type in which the aforementioned disadvantages are absent and which in terms of both taste and price is acceptable and attractive, has no unpleasant odor, promotes health and is easy and convenient to ingest, and which guarantees a sufficiently high dosing.

This problem is solved through the inventional foodstuff, which is characterized in that it contains at least a combination of the following ingredients:

A) at least one multiple unsaturated omega-3-fatty acid and/or its ester with a prophylactic and/or healing effect; and B) one or several vitamins and/or provitamins with the same or a further prophylactic or healing effect.

A preferred manufacturing process forms another object of the invention.

The inventional foodstuff is available preferably in the form of a fruit and/or vegetable juice or of a beverage prepared thereof, and is distinguished by a pleasant taste and flavor. Thus, it can be consumed easily and without repugnance. The natural taste of the multiple omega-3-fatty acid forming the component A is masked by the remaining ingredients of the foodstuff or is eliminated through the interaction between the components A and B, specifically the mutual stabilization, which will be addressed yet in greater detail in the following, so that it is not noticed at all.

The components A and B are suitably used in quantities which in terms of disease are prophylactic and/or healing.

These quantities are variable and, if desired, can be adapted to the nutritional offer in the region where the foodstuff is offered for consumption. For instance, in a region where much fish is consumed anyhow, the share of the component A can be reduced and, conversely, in a region where only little fish is consumed, it can be increased. Besides, the vitamin offer can be varied and adapted to living conditions, so that the occurrence of location-specific deficiencies can be effectively prevented.

The inventional foodstuff is normally offered packaged, for instance in bottles, with each package favorably containing a daily dose of components A and B. The daily dose can be consumed in portions, for example in two to four portions, where the occasional consumption of greater amounts is by no means harmful.

The inventional foodstuff contains multiple unsaturated omega-3-fatty acids forming the component A, preferably eicosanoic pentaene acid and/or docosanoic hexaene acid or their esters, for instance as ingredient of fish oil. Depending on type of fish and location at which the fish has lived, the content of the said acids amounts to 20–33%, based on the total amount of fat in the fish oil. But the said acids may be available also in pure form, provided the pure acids are available in sufficient quantities and at an adequate price.

As component B, the inventional foodstuff contains preferably vitamin A or its beta-carotene precursor, vitamin C, vitamin E and/or retinoids. The said vitamins and provitamins may be contained wholly or partly, specifically in the case of a fruit or vegetable juice, in the juice or juice mixture forming the base and, as the case may be, may only be supplemented. To accomplish a sufficiently high dosing, however, they are preferably admixed to the juice or juice mixture forming the base. Since in the case of vitamin A an overdosing may result in undesirable and, as the case may be, harmful side effects, the foodstuff contains preferably, instead of vitamin A, its beta-carotene precursor, which the body converts to vitamin A in the required quantities while the rest is excreted. The retinoids are close relatives of vitamin A with essentially the same effect. The development of retinoids is still under way, the objective being to obtain retinoids with minimal side effects.

The component B supplements effectively the component A in the prophylaxis of cardiovascular diseases and, furthermore, is significant specifically for a cancer prophylaxis. This all the more as the amount of component A contained in the foodstuff of the said type is not sufficient for an effective prophylaxis of cancer but cannot readily be increased arbitrarily.

In addition to the components A and B, the foodstuff contains preferably sugar, sweeteners and/or flavoring or aromatic substances. The latter serve to mask the unpleasant natural taste or odor associated with the omega-3-fatty acids, which normally are employed in the form of fish oil, and to lend the foodstuff a taste that is pleasant also to sensitive palates and noses. A content of flavoring and/or aromatic substances is recommended specifically when the taste intensity of the other ingredients combined with the fish oil is too weak for masking the fish oil taste. The selection of suitable flavoring and aromatic substances resides within the scope of expert knowledge and can be made with the aid of trade literature and tabular works, with preference going normally to products of natural origin.

Besides, the foodstuff may contain further additives with prophylactic or healing effect, for instance vitamin D, in order to remedy deficiencies that occur in the region in which the foodstuff is to be consumed.

In case the foodstuff is available in the form of a fruit and/or vegetable juice, it contains suitably additives which increase the viscosity, so as to improve storage stability, specifically preventing an undesirable separation of the juice or juice mixture used as an emulsion, which separation would adversely affect the appearance of the foodstuff, and to increase the oxidation stability. Suitable additives for raising the viscosity, e.g., are fruit juice concentrates and pectins.

To improve the storage stability, specifically the stability against oxidizing effects, a content of antioxidants is recommended, especially when the foodstuff is to be offered in a sterilized form.

As already mentioned, the package size in the case of the foodstuff offered in packaged form should be so dimensioned that each individual package, for instance a bottle in the case of a beverage on the basis of fruit or vegetable juice, contains a daily dose of components A and B, with the daily portion amounting for example to one-third liter juice, juice mixture or beverage made using these.

In the case of a preferred fruit juice beverage, a daily portion of ⅓ liter has the following composition:

| | |
|---|---|
| orange juice | 0.3 liter |
| sugar (saccharose) | 11 grams |
| natural orange aroma | 1.8 grams |
| fish oil | 750 milligrams |
| vitamin C | 250 milligrams |
| vitamin E | 60 milligrams |
| beta-carotene | 15 milligrams |
| water to make | ⅓ liter. |

Another preferred beverage on the basis of fruit and/or vegetable juice contains in 525 grams of ready-to-consume beverage

| | |
|---|---|
| fruit juice base (with about 90% juice) | 472 grams |
| fish oil | 1300 milligrams |
| beta-carotene and | 23 milligrams |
| sweeteners, sugar, orange aroma. | |

The production process for the inventional foodstuff will be described hereafter on the example of producing a beverage on the basis of a fruit and/or vegetable juice. The procedure in the application of the process is such that a) the fatty acids and/or their esters or the fish oil containing these are made available in the form of a dry powder;

b) vitamin E and a partial amount of the entire amount of the beta-carotene are added in the form of a dry powder and this mixture is mixed with vitamin C which is on hand in dry form;

c) the dry mixture obtained in step b) is stirred into fruit and/or vegetable juice heated to at least 40° C. or, to begin with, is stirred into water heated to at least 40° C. followed by adding it to the fruit and/or vegetable juice heated to the same temperature, the amount of fruit and/or vegetable juice amounting to more than 60% of the final product; and d) the resulting mixture is brought up to 100% using water, and bottled for shipping and/or marketing.

In this process it is essential that the fat-soluble components—in step a) the fatty acids and/or their esters or fish oil containing these, and in step b) the vitamin E and the beta-carotene—are used in the form of a dry powder. This makes it possible to avoid disadvantages resulting from the different dissolution behavior of the individual components.

As generally known, some of the components forming the beverage are water-soluble, for instance vitamin C, others only miscible with water, while a part is soluble in fat. As a result, the components in the beverage will not readily distribute themselves uniformly, and the fat-soluble components will float on top in the form of oil puddles when the beverage is set aside. This would greatly affect the appearance of the beverage, leading to rejection by the consumer. Using dissolving agents and/or dispersants or emulsifiers yields normally only short-term success and is questionable in conjunction with foodstuffs. Using fat-soluble components in dry form provides the possibility to produce a beverage where the said disadvantages will not occur and which even at prolonged storage, for instance nine to twelve months, will retain its homogeneity and its attractive appearance. Besides, it is possible to achieve in this way that the natural odor or natural taste of the fish oil or of the multiple unsaturated omega-3-fatty acids in the finished beverage will not be noticeable, or only little, and that also a retroactive, unpleasant eructation will be avoided. In making the beverage, the fruit or vegetable juice is preferably used in a quantity which suitably corresponds to more than 60% of the total amount of the final product. Added to the fruit or vegetable juice, additionally, may be agents that increase the viscosity, for instance before stirring the powdery material from step b) in. The selection of the agents for increasing the viscosity that are to be used in the specific case is within the scope of expert knowledge. At this stage, also sugar, sweeteners, flavoring or aromatic substances may be added, as far as their addition is desirable. Besides, the addition of sugar may cause a slight increase of the viscosity, thereby preventing the risk of an initial oxidation of the ingredients of the beverage prior to obtaining balanced solution, since the mobility of the molecules contained in the juice or juice mixture is reduced with increasing viscosity, thereby impeding oxidation reactions both in the production stage and in the future storage of the beverage. Since oxidation losses in the range of 10% during the production and bottling phase cannot be avoided, it is recommended to allow for these losses in providing the quantities of individual components.

A high share of juice in the finished beverage, for instance of more than 60%, has still another positive aspect: it ensures a permanent turbidation stability also with a relatively high share of fish oil, for instance 750 mg on ⅓ liter, in keeping with the recipe given above. Experiments have shown that beverages with a lower share of juice will with an equally high share of fish oil not display a satisfactory long-term turbidation stability. It is assumed that a suitable balancing of the components A and B leads to an equilibrium which permanently ensures turbidation stability. The latter contributes to an attractive appearance of the beverage and, thus, to its acceptance by the consumer.

The addition of small amounts of antioxidants serves the same purpose. The addition of the antioxidant to the juice or juice mixture may be carried out simultaneously with the addition of the other components or immediately thereafter, whereupon the finished mixture may subsequently or prior to bottling be sterilized. Besides, it is recommended to homogenize the beverage before bottling, since in this way it is possible to suitably influence its turbidation stability and, thus, its appearance. Storage stability is also enhanced by protecting the beverage until its consumption from the effects of light.

Due to the known properties of the components A and B it was by no means to be expected that their combination and mutual balancing would lead to a foodstuff whose properties in view of stability to oxidizing effects, permanent turbidation stability, storage stability, vitamin content, appearance, taste and flavor have in comparison to these properties of the individual components been improved to a degree exceeding by far that given by the sum of properties of the individual components and which can be explained only by a synergistic interaction. Not least, the favorable improvement is attributable to a mutual protective effect resulting from the combination of individual components. For example, it is noted that the vitamin content of the combination, disregarding its initial slight loss in the production phase, remains unchanged also at prolonged storage, for instance of nine to twelve months. This was by no means to be expected since, as is generally known, the vitamin content in fruit and vegetable normally drops rapidly already shortly after harvesting, due to breakdown reactions, and approaches zero already after a relatively short time. It may be assumed that the individual components mutually stabilize themselves, with particular significance to be ascribed apparently to beta-carotene and vitamin C.

Far more significant and to be emphasized particularly, however, is the fact that the physiological effects of the components A and B complement one another synergistically, so that the prophylactic and/or healing effect achieved through the inventional foodstuff is considerably greater than was to be expected due to the inherent effects of the individual components. Furthermore, the combination effect causes an extraordinary broadening of the spectrum of effects and applications, especially in conjunction with the application in the realm of prophylaxis and therapy in the case of cardiovascular diseases and in the realm of cancer prophylaxis and cancer therapy. Owing to the complexity of the said diseases comprising a number of locally and pathologically different illnesses, however, a broad spectrum of effects and applications is an essential prerequisite for a successful prophylaxis and/or therapy. Especially in the case of cancer it must not be overlooked that the various types of cancer differ not only by their location of occurrence but also by genesis and pathology. Therefore, an effective cancer prophylaxis can be achieved only through an interaction of several components which complement and reinforce one another, such as is the case with the inventional foodstuff, on account of the observed and doubtless present synergism. The ingestion of a single vitamin or unsaturated omega-3-fatty acid achieves normally only a very limited effect, in a way such that the individual component by itself will unfold its effect only in a very narrow range, for instance only at a specific syndrome, whereas with another, similar syndrome it is hardly or not at all effective. This is disadvantageous especially in the case of cancer prophylaxis and cancer therapy, since exactly with this disease there are considerable differences with regard to the type, location of occurrence, genesis and pathology. Therefore, it was extraordinarily surprising and by no means foreseeable that a prophylactic and/or healing effect foodstuff with such a broad spectrum of applications and effects could be provided by the combination of components A and B and by the selection and combination of the ingredients forming these components and an essential characteristic of the present invention.

This opens in a unique way the possibility of providing the body in sufficient quantities and in a simple and convenient way with the active ingredients necessary for an effective prophylaxis, namely unsaturated omega-3-fatty acids for one, and vitamins for another, without risking undesirable side effects.

What is claimed is:

1. A foodstuff being present in the form of a fruit juice and/or vegetable juice or a beverage which at continued ingestion displays a prophylactic and/or therapeutic effect for prevention and/or treatment of cardiovascular diseases and/or cancer comprising at least a combination of the following components:

A) at least one multiple unsaturated omega-3-fatty acid and/or its esters with a prophylactic and/or therapeutic effect; and B) one or several vitamins or provitamins with the same or a further prophylactic or therapeutic effect; and
wherein components A and B are contained in a quantity being effective in a synergistic manner in the prophylaxis and/or treatment of cardiovascular diseases or the prophylaxis of cancer; and
wherein component A is included in the form of dry, powdered fish oil.

2. The foodstuff according to claim 1, having the following composition:

| | |
|---|---|
| orange juice | 0.3 liter |
| sugar (saccharose) | 11 grams |
| natural orange aroma | 1.8 grams |
| dry powdered fish oil | 750 milligrams |
| vitamin C | 250 milligrams |
| vitamin E | 60 milligrams |
| beta-carotene | 15 milligrams |
| water to give | ⅓ liter. |

3. The foodstuff according to claim 1, wherein said foodstuff is available in packaged form, with each package containing a dose of the components (A) and (B).

4. The foodstuff according to claim 1, wherein said foodstuff contains vitamin A or beta-carotene, vitamin C, vitamin E and/or retinoids as component (B).

5. The foodstuff according to claim 1, wherein said foodstuff further contains sugar, sweetener and/or flavoring or aromatic substances.

6. The foodstuff according to claim 1, wherein said foodstuff contains fruit juice concentrates.

7. The foodstuff according to claim 1, wherein said foodstuff is in sterilized form.

8. A process for the production of a foodstuff being present in the form of a fruit juice and/or vegetable juice or a beverage which at continued ingestion displays a prophylactic and/or therapeutic effect for prevention and/or therapy of cardiovascular diseases and/or cancer comprising at least a combination of the following components:

A) at least one multiple unsaturated omega-3-fatty acid and/or its esters with a prophylactic and/or therapeutic effect; and B) one or several vitamins or provitamins with the same or a further prophylactic or therapeutic effect; and
wherein components A and B are contained in a quantity being effective in a synergistic manner in the prophylaxis and/or treatment of cardiovascular diseases or the prophylaxis of cancer;
said process comprising the steps of:
a) providing components A in the form of fish oil in the form of a dry powder;
b) mixing components A, B and the remaining components to obtain the foodstuff.

9. The process according to claim 8, wherein component B comprises vitamin E, beta-carotene and vitamin C.

10. The process according to claim 8, wherein a viscosity-increasing agent is added at step (b).

11. The process according to claim 8, wherein a sugar, sweetener, flavouring or aromatic substances are added at step (b).

12. The process according to claim 8, wherein the resulting mixture is homogenized.

13. The process according to claim 8, wherein the foodstuff is sterilized before bottling, facultatively under addition of an antioxidant.

14. The use of the process according to claim 8 to produce an orange juice beverage of the following composition:

| | |
|---|---|
| orange juice | 0.3 liter |
| sugar (saccharose) | 11 grams |
| natural orange aroma | 1.8 grams |
| dry powdered fish oil | 750 milligrams |
| vitamin C | 250 milligrams |
| vitamin E | 60 milligrams |
| beta-carotene | 15 milligrams |
| water to give | ⅓ liter. |

* * * * *